(12) United States Patent
Schankula et al.

(10) Patent No.: US 12,405,257 B2
(45) Date of Patent: Sep. 2, 2025

(54) METHOD FOR OPERATING A NITROGEN OXIDE SENSOR

(71) Applicant: Mercedes-Benz Group AG, Stuttgart (DE)

(72) Inventors: Herbert Schankula, Esslingen (DE); Nhat Phan, Weinstadt (DE); Rainer Hegemann, Ludwigsburg (DE); Matthias Hoelz, Ludwigsburg (DE); Yvonne Binder, Hemmingen (DE)

(73) Assignee: Mercedes-Benz Group AG, Stuttgart (DE)

( * ) Notice: Subject to any disclaimer, the term of this patent is extended or adjusted under 35 U.S.C. 154(b) by 0 days.

(21) Appl. No.: 18/290,635

(22) PCT Filed: Jul. 4, 2022

(86) PCT No.: PCT/EP2022/068400
§ 371 (c)(1),
(2) Date: Jan. 19, 2024

(87) PCT Pub. No.: WO2023/001530
PCT Pub. Date: Jan. 26, 2023

(65) Prior Publication Data
US 2024/0255482 A1 Aug. 1, 2024

(30) Foreign Application Priority Data

Jul. 22, 2021 (DE) ...................... 10 2021 003 759.6

(51) Int. Cl.
*G01N 33/00* (2006.01)
*F01N 11/00* (2006.01)

(52) U.S. Cl.
CPC ....... *G01N 33/0062* (2013.01); *F01N 11/007* (2013.01); *F01N 2550/02* (2013.01); *G01N 33/0068* (2024.05)

(58) Field of Classification Search
CPC ........... G01N 33/0062; G01N 33/0068; G01N 33/0037; F01N 11/007; F01N 2550/02;
(Continued)

(56) References Cited

U.S. PATENT DOCUMENTS 9,010,087 B1 * 4/2015 Upadhyay ............. F02D 41/222
60/276
10,920,645 B2 2/2021 Yoo et al.
(Continued)

FOREIGN PATENT DOCUMENTS

DE 103 09 422 A1 9/2004

OTHER PUBLICATIONS

International Search Report (PCT/ISA/210) issued in PCT Application No. PCT/EP2022/068400 dated Sep. 13, 2022 (2 pages).

*Primary Examiner* — Matthew T Largi
(74) *Attorney, Agent, or Firm* — Crowell & Moring LLP

(57) ABSTRACT

A method for operating a nitrogen oxide sensor of an internal combustion engine. When, for a number greater than 1 of operating cycles each including exactly two directly consecutive periods of time, where during a respective first of the periods of time the engine is in fired operation and during the respective second period of time a fired operation of the engine ceases, it is determined that an arithmetic mean of the first periods of time is less than a first threshold value and an arithmetic mean of the second periods of time is less than a second threshold value, a special overrun operating state of a computer is set, where after deactivation of the engine, the computer is kept activated in the special overrun operating state for a longer overrun period, where the nitrogen oxide sensor is kept in a state of operating readiness during the overrun period.

6 Claims, 1 Drawing Sheet

(58) Field of Classification Search
CPC .............. F01N 2560/026; F01N 11/00; F02N 11/00–11/087
See application file for complete search history.

(56) References Cited

U.S. PATENT DOCUMENTS

| | | | |
|---|---|---|---|
| 2007/0137177 A1* | 6/2007 | Kittelson | F02D 41/008 60/285 |
| 2016/0069243 A1* | 3/2016 | Hegemann | F01N 3/208 60/274 |
| 2017/0010236 A1* | 1/2017 | Sakashita | F01N 11/007 |
| 2019/0376425 A1* | 12/2019 | Kato | F01N 3/085 |
| 2020/0088673 A1* | 3/2020 | Koyabu | F02D 41/222 |

* cited by examiner

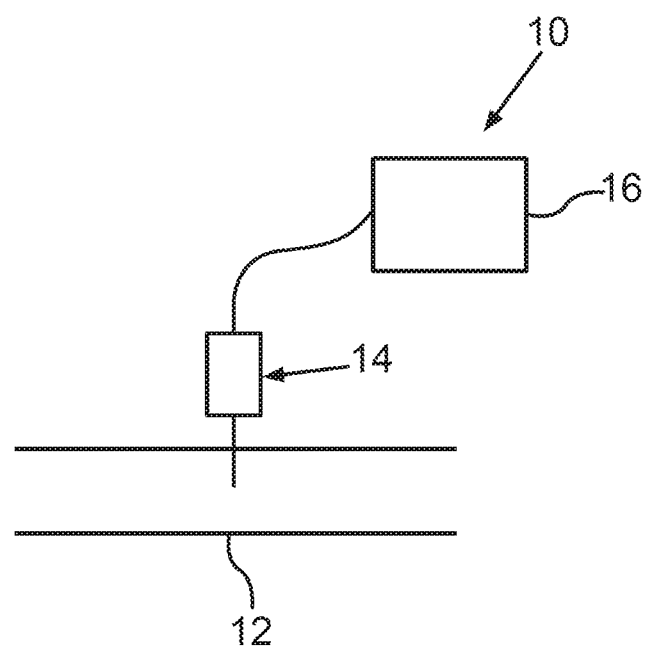

METHOD FOR OPERATING A NITROGEN OXIDE SENSOR

BACKGROUND AND SUMMARY OF THE INVENTION

The invention relates to a method for operating a nitrogen oxide sensor.

Such a method for operating a nitrogen oxide sensor can for example be taken as known from DE 103 09 422 A1. The nitrogen oxide sensor is designed to record nitrogen oxide contained in the exhaust gas of an internal combustion engine, in particular of a motor vehicle. The nitrogen oxide is also described as NOx, such that the nitrogen oxide sensor is also described as an NOx sensor. In the method, an electronic computer also described as a control device is designed to receive an, in particular electrical, signal which can be provided by the sensor and which characterises the nitrogen oxide recorded by means of the sensor.

The object of the invention is to develop a method of the kind specified in the introduction such that a particularly advantageous operation can be implemented.

To develop a method of the kind specified herein such that a particularly advantageous operation can be implemented, it is provided according to the invention that if, for a number greater than one, also labelled n, of operating cycles each comprising exactly two directly consecutive periods of time, wherein during a respective first of the periods of time of the respective operating cycle the internal combustion engine is in fired operation and during the respective second period of time of the respective operating cycle a fired operation of the internal combustion engine ceases, it is determined that the arithmetic mean, i.e., an average also described as an average value of the first periods of time of the n operating cycles is less than a first threshold value and the arithmetic mean, i.e., an average also described as an average value of the second period of time of the n operating cycles is less than a second threshold value, a special overrun operating state of the electronic computer, which is also described as a control device, is set. After and despite deactivation of the internal combustion engine, the electronic computer (control device) is kept activated in the special overrun operating state for a longer overrun period in relation to a normal operating state which is different from the special overrun operating state of the electronic computer, and which preferably directly follows the deactivation of the internal combustion engine, whereby the nitrogen oxide sensor is ready for operation, i.e., is kept in a state of operating readiness, in particular continuously, during the overrun period, in which state of operating readiness the nitrogen oxide sensor is capable of recording nitrogen oxide and providing the signal.

If the internal combustion engine, for example designed as a diesel engine, is activated and deactivated several times alternately, the invention in particular makes it possible to avoid a distortion of an ammonia fill level model for calculating a fill level of ammonia in an SCR catalyst. An alternating activation and deactivation of the internal combustion engine several times one after the other is also described as a short-term operation of the internal combustion engine. Such a short-term operation arises, for example, if the internal combustion engine is used to drive a motor vehicle, for example designed as a motor car, and in particular, for example, if the motor vehicle is used as a delivery vehicle for delivering packages or similar cargo. If the internal combustion engine is designed as a diesel engine, then the motor vehicle is a diesel vehicle. Preferably, the motor vehicle has an injection device, by means of which a reducing agent can be introduced into the exhaust gas to denitrify the exhaust gas. The reducing agent is preferably an aqueous urea solution, which is designed to provide ammonia (NH3). In the context of a selective catalytic reduction (SCR), nitrogen oxides contained in the exhaust gas can react with the provided ammonia to form nitrogen and water, whereby the nitrogen oxides contained in the exhaust gas are at least partially removed from the exhaust gas, and the exhaust gas is thus denitrified. The SCR catalyst is catalytically active for the selective catalytic reduction, such that the SCR catalyst catalytically causes and/or supports the selection catalytic reduction. Ammonia provided by the reducing agent introduced into the exhaust gas, which ammonia does not react with nitrogen oxide contained in the exhaust gas and to form water and nitrogen, i.e., is not converted, is also described as excess ammonia, wherein excess ammonia can accumulate in the SCR catalyst. A quantity of excessive ammonia contained in the SCR catalyst is also described as a fill level, ammonia fill level or NH3 fill level of the SCR catalyst. The previously specified ammonia fill level model, also described as an NH3 fill level model, is used to calculate the fill level. The invention makes it possible to avoid a distortion of an NH3 fill level model or a distortion of the fill level calculated by means of the NH3 fill level model.

Because the overrun period in the special overrun operating state is longer than in the normal operating state, the overrun can be lengthened by the invention. If the electronic computer is kept activated despite and after the deactivation of the internal combustion engine, the electronic computer is operated in an overrun. Because, during the overrun period, the nitrogen oxide sensor and the control device (electronic computer) can be in a state of operating readiness, and because the nitrogen oxide sensor is also described as a probe or NOx probe, an extended NOx probing readiness is implemented by the invention in relation to the normal operating state. Excessive NH3 fill level model deviations can thus be avoided. In other words, a particularly high model quality of the NH3 fill level model can be implemented.

In an advantageous embodiment of the invention, it is provided that the number is greater than 5.

In an advantageous embodiment of the invention, it is provided that the number is less than 20.

In an advantageous embodiment of the invention, it is provided that the first threshold value is 20 minutes at most.

In an advantageous embodiment of the invention, it is provided that the second threshold value is 1 minute at most.

In an advantageous embodiment of the invention, it is provided that in the special overrun operating state, the overrun period is at least 5 minutes.

Further advantages, features and details of the invention result from the following description of a preferred exemplary embodiment and with reference to the drawing. The features and combinations of features previously specified in the description and the features and combinations of features specified in the following description of FIGURE and/or shown alone in the single FIGURE can be used not only in the specified combination, but also in other combinations or in isolation, without leaving the scope of the invention.

BRIEF DESCRIPTION OF THE DRAWING

The single FIGURE shows a section of a schematic depiction of an exhaust system for an internal combustion engine of a motor vehicle.

DETAILED DESCRIPTION OF THE DRAWING

The FIGURE shows a section of a schematic depiction of an exhaust system 10 for an internal combustion engine of a motor vehicle. This means that the motor vehicle, for example designed as a motor car, in particular as a commercial vehicle, has the internal combustion engine and the exhaust system 10 in its completely produced state, and can be driven by means of the internal combustion engine. The internal combustion engine is fired, and can thus be operated in a fired operation. During the fired operation, combustion processes take place in the internal combustion engine. In the respective combustion process, a mixture of fuel and air is combusted. This results in exhaust gas of the internal combustion engine, the exhaust gas of which can flow through the exhaust system 10, in particular through an exhaust pipe 12 of the exhaust system 10. For example, the exhaust system 10 comprises an SCR catalyst which is not depicted in the FIGURE, which can be flowed through by the exhaust gas. If the internal combustion engine, and thus the fired operation are deactivated, then a fired operation of the internal combustion engine ceases at least temporarily, such that no combustion processes take place in the internal combustion engine.

The exhaust gas of the internal combustion engine can contain nitrogen oxides (NOx). In order to implement a particularly low-emission operation, at least one dosing device not depicted in the FIGURE is for example provided, by means of which a reducing agent can be introduced, in particular injected, into the exhaust gas. The reducing agent is for example an aqueous urea solution, which provides ammonia (NH3) if it is introduced into the hot exhaust gas. In the context of a selective catalytic reduction (SCR), at least a part of the nitrogen oxides contained in the exhaust gas reacts with the provided ammonia to form nitrogen and water, whereby at least a part of the nitrogen oxides contained in the exhaust gas is removed from the exhaust gas, and the exhaust gas is thus denitrified. The previously specified SCR catalyst is catalytically effective for the specified selective catalytic reaction.

The exhaust gas system 10 also comprises at least one nitrogen oxide sensor 14 by means of which the nitrogen oxides contained in the exhaust gas can be recorded. In addition, the nitrogen oxide sensor 14, also simply described as a sensor, can provide an, in particular electrical, signal. The signal characterises the nitrogen oxides recorded by means of the sensor. In particular, the signal characterises a quantity of the nitrogen oxides recorded by means of the sensor. A control device 16 is further provided, which is an electronic computer. The control device 16 is designed to receive the signal provided by the sensor. The control device 16 can be part of an engine control device for controlling and/or regulating the internal combustion engine. In the following, a method for operating the nitrogen oxide sensor 14 is described.

To be able to implement a particularly advantageous operation, it is provided in the method that if, for a number greater than 1, also labelled n, of operating cycles of the internal combustion engine each comprising exactly two directly consecutive periods of time, wherein during a respective first of the periods of time of the respective operating cycle the internal combustion engine is in fired operation and during the respective second period of time of the respective operating cycle a fired operation of the internal combustion engine ceases, it is determined that the arithmetic mean of the first periods of time of the n operating cycles is less than a first threshold value and the arithmetic mean of the second periods of time of the n operating cycles is less than a second threshold value, a special overrun operating state of the electronic computer (control device 16) is set, wherein after and despite a deactivation of the internal combustion engine, the control device 16 is kept activated in the special overrun operating state for a longer overrun period in relation to a normal operating state which is different from the special overrun operating state of the control device 16, whereby the nitrogen oxide sensor 14 is kept in a state of operating readiness during the overrun period, in which state of operating readiness the nitrogen oxide sensor 14 is capable of recording nitrogen oxide and providing the signal. In particular, n describes a positive integer. Preferably, n is 10, such that for example the number of operating cycles also described as driving cycles is for example 10. The following facts and considerations are in particular the basis of the method:

In a manner of driving, i.e., in an operation of the motor vehicle with short engine running times, interrupted by short engine shutdown times, it can conventionally be the case that after an activation, also described as an engine start, of the internal combustion engine, the nitrogen oxide sensor 14 is temporarily non-operational, i.e., has no state of operating readiness, also described as probing readiness, and thus cannot measure nitrogen oxides contained in the exhaust gas, in particular nitrogen oxide emissions of the internal combustion engine. The respective, previously specified engine running time should be understood to mean an interval of time in which the internal combustion engine is activated, i.e., is in fired operation. The respective, previously specified engine shutdown time should be understood to mean an interval of time in which, in particular continuously, a fired operation of the internal combustion engine ceases, and thus the internal combustion engine, and thus the fired operation of the internal combustion engine are deactivated.

Conventionally, the nitrogen oxide sensor 14 comes into operational readiness only at or after a first point in time, wherein a first period of time lies between the first point in time and the engine start, which can for example be up to 10 to 15 minutes. The first point in time for example characterises an end of a dew point. In other words, it is for example assumed that no more condensation is contained in the exhaust system 10 at the first point in time. In particular, it is conceivable that the nitrogen oxide sensor 14 conventionally only comes into operational readiness after the first point in time and at a second point in time following the first point in time, wherein there can be a second period of time between the first point in time and the second point in time, which can for example be around 100 seconds. During the second period of time, which follows the first period of time, a heating phase takes place, for example, in which, for example, the nitrogen oxide sensor 14, also described as a probe, nitrogen oxide probe or NOx probe, is heated, in particular for example to around 800 degrees Celsius. During the first period of time and the following second period of time, the nitrogen oxide sensor 14 is then not operationally ready, and thus cannot measure nitrogen oxides contained in the exhaust gas, but the internal combustion engine runs in a fired manner during the first period of time and during the second period of time, and for example drives the motor vehicle, such that for example the motor vehicle is driven during the first period of time and the second period of time. The first period of time and the second period of time, for example, form a total time, during which the nitrogen oxide sensor 14 cannot measure any nitrogen oxides in the exhaust gas. During the total time, the reducing agent is not introduced into the exhaust gas depending on measured values of the nitrogen oxide sensor 14, because no measured values or no meaningful values are provided by the latter during the total time, and instead, during the total time, the reducing agent is introduced into the exhaust gas depending on a first computing model, which is also simply described as a first model or NOx raw emissions replacement model. However, the first model is not excessively accurate, and in some circumstances can lead to an excessively high quantity of the reducing agent being introduced into the exhaust gas due to overestimation. This should be understood to mean that the quantity of the reducing agent introduced into the exhaust gas is greater than is required to denitrify the exhaust gas, meaning that not all of the ammonia provided by the reducing agent is converted. If this takes place many times one after the other, as, for example, in a short-term operation, i.e., as can be the case when the internal combustion engine is activated and deactivated very frequently in succession, this can result in an unnecessarily high dose of the reducing agent and due to the excessively high dose, at some point after a relatively long period of time, a false result of a diagnosis for checking the SCR catalyst or a diagnosis for checking the nitrogen oxide sensor 14 can consequently arise. The cause is that the actual nitrogen oxide emissions of the internal combustion engine are lower than the values calculated, and thus predicted by the first model, also described as a NOx model. Because, however, in the absence of the operational readiness of the nitrogen oxide sensor 14, dosing is carried out, i.e., the reducing agent is introduced into the exhaust gas, depending on the first model, this can lead to an undesirable, increased amount of the reducing agent being introduced into the exhaust gas, and thus to a system for example comprising at least one SCR catalyst. Because the internal combustion engine provides less nitrogen oxides than is calculated by means of the first model, not all of the dosed reducing agent is used up by the nitrogen oxides contained in the exhaust gas, such that excess reducing agent or ammonia provided by the latter is stored in the SCR catalyst. A quantity of ammonia stored in the SCR catalyst is also described as a fill level, ammonia fill level or NH3 fill level of the SCR catalyst. Using a second computing model, which is also described as a second model or fill level model or NH3 fill level model or ammonia fill level model, the fill level of the SCR catalyst can be calculated. The fill level model, however, cannot recognize the previously described effect. In other words, the fill level model cannot recognize that an excessive quantity of the reducing agent has been introduced into the exhaust gas due to the short-term operation and that excessive ammonia has consequently been stored in the SCR catalyst. The fill level rather assumes that at least almost all of the self-dosed reducing agent is used up, and is thus converted. Because the unused, and thus excessive reducing agent or ammonia is stored in the SCR catalyst, however, the fill level model calculates the fill level only very imprecisely. Downstream functions, which rely on the fill level calculated by means of the second model, in particular for a dose or an OBD (on-board diagnosis), can thus make incorrect decisions.

The previously specified problems and disadvantages can be avoided via the invention. Statistics on how many short engine operating times, i.e., engine running times, are followed by short engine shutdown phases, and thus engine shutdown times, are kept, so-to-speak, by the method. If a manner of operating with many such short-term operating phases is recognized, then the overrun of the control device 16, also described as a control device overrun, is in particular lengthened in relation to the normal operating state, wherein the nitrogen oxide sensor 14 is connected to the control device 16, in particular via signal transmitting technology. For example, the control device 16 is a control device by means of which the introduction of the reducing agent into the exhaust gas is carried out, in particular controlled or regulated. In particular, it can be provided that the control device 16 calculates the quantity of the reducing agent to be introduced into the exhaust gas. As an alternative or in addition, the previously specified diagnosis of the nitrogen oxide sensor 14 and/or the SCR catalyst is for example carried out or calculated by means of the control device 16.

The lengthened overrun of the control device 16 in relation to the normal operating state in particular means the following: even if the driver of the motor vehicle ends the ignition of the motor vehicle, and thus the internal combustion engine or its fired operation, by switching off the so-called terminal 15, then the control device 16 remains awake, i.e., activated, so-to-speak, and the nitrogen oxide sensor 14 maintains its state of operating readiness, in particular without interruption, which the nitrogen oxide sensor has also taken up before the internal combustion engine was deactivated.

In the method, the following is in particular provided: it is checked whether a so-called short operation is present, which is also described as a short-term operation, and specifically depending on how long the internal combustion engine, also described as an engine, was in operation after its last engine start, and depending on a duration of the last engine shutdown time, and thus how long the engine was deactivated since the last operation. If, for example, in the last n operating cycles, which are also described as driving cycles, the average time, also described as an average operating time, during which the internal combustion engine is in its fired operation is shorter than the first threshold value, and if the average time of the engine deactivation times is shorter than the second threshold value, then it is communicated that the previously specified short operation is present. The respective driving cycle is defined in the OBD as an OBD driving cycle.

In particular, a status is set that a short operation is present. If the status is set, then the overrun of the control device 16, also described as a control device overrun, is lengthened for example to 5 minutes or more in comparison with the normal operating mode, wherein during the overrun, i.e., during the overrun period, the state of operating readiness of the nitrogen oxide sensor 14 is maintained, such that if the internal combustion engine is started again within the overrun period, as, for example, in 5-minute operation, the nitrogen oxide sensor 14 is immediately able to measure nitrogen oxides contained in the exhaust gas, i.e., to carry out measurements and thus to measure the nitrogen oxides contained in the exhaust gas and to provide the signal characterizing the nitrogen oxides measured by means of the nitrogen oxide sensor 14, such that the reducing agent is introduced into the exhaust gas, i.e., can be dosed, in the event of re-starting, not depending on the first model (NOx raw emissions replacement model), but depending on the signal, i.e., depending on the nitrogen oxides measured by means of the sensor. If it is recognized that the short operation is no longer present, then no lengthened overrun is set with an increased state of operating readiness of the sensor when the internal combustion engine is deactivated, i.e., the terminal 15 is switched off. The control device 16 is then, for example, in its normal operating state, in which the overrun period is shorter than in the special overrun operating state. In addition, the previously specified status can be reset if a successful particulate filter regeneration has taken place. Because high exhaust gas temperatures lead to ammonia being discharged out of the SCR catalyst, the fill level model can provide correct values for the fill level again directly after a successful particulate filter regeneration.

LIST OF REFERENCE CHARACTERS 10 exhaust system
12 exhaust pipe
14 nitrogen oxide sensor
16 control device

The invention claimed is:

1. A method for operating a nitrogen oxide sensor for recording nitrogen oxide contained in exhaust gas of an internal combustion engine, in which an electronic computer is configured to receive a signal provided by the nitrogen oxide sensor, wherein the nitrogen oxide recorded by the nitrogen oxide sensor characterises the signal, the method comprising:

setting a special overrun operating state of the electronic computer when, for a number greater than 1 of operating cycles each comprising exactly two directly consecutive periods of time, wherein during respective first periods of time of the respective operating cycle the internal combustion engine is in fired operation and during the respective second periods of time of the respective operating cycle a fired operation of the internal combustion engine ceases, it is determined that an arithmetic mean of the first periods of time is less than a first threshold value and an arithmetic mean of the second periods of time is less than a second threshold value;

deactivating the internal combustion engine;

keeping the electronic computer activated in the special overrun operating state, after the deactivating of the internal combustion engine, for a longer overrun period in relation to an overrun period of a normal operating state;

keeping the nitrogen oxide sensor in a state of operating readiness during the longer overrun period; and recording nitrogen oxide by the nitrogen oxide sensor and providing the signal by the nitrogen oxide sensor to the electronic computer when the nitrogen oxide sensor is in the state of operating readiness during the longer overrun period.

2. The method according to claim 1, wherein the number is greater than 5.

3. The method according to claim 1, wherein the number is less than 20.

4. The method according to claim 1, wherein the first threshold value is 20 minutes at most.

5. The method according to claim 1, wherein the second threshold value is 1 minute at most.

6. The method according to claim 1, wherein in the special overrun operating state, the longer overrun period is at least 5 minutes.

* * * * *